US009207172B2

(12) United States Patent
Seebaluck et al.

(10) Patent No.: US 9,207,172 B2
(45) Date of Patent: Dec. 8, 2015

(54) VELOCITY SURVEY WITH POWDERIZER AND AGENT FLOW INDICATOR

(75) Inventors: Dharmendr Len Seebaluck, Wake Forest, NC (US); Robert Glaser, Stella, NC (US); Mark P. Fazzio, Wilson, NC (US); Louis W. Rance, Lucama, NC (US); Brian Powell, Berkshire (GB)

(73) Assignee: KIDDE TECHNOLOGIES, INC., Wilson, NC (US)

( * ) Notice: Subject to any disclaimer, the term of this patent is extended or adjusted under 35 U.S.C. 154(b) by 38 days.

(21) Appl. No.: 13/251,495

(22) Filed: Oct. 3, 2011

(65) Prior Publication Data

US 2012/0300192 A1 Nov. 29, 2012

Related U.S. Application Data

(60) Provisional application No. 61/490,193, filed on May 26, 2011.

(51) Int. Cl.

| | |
|---|---|
| ***G01P 3/36*** | (2006.01) |
| ***G01N 21/53*** | (2006.01) |
| ***G01F 1/708*** | (2006.01) |
| ***G01F 1/74*** | (2006.01) |

(52) U.S. Cl.
CPC ............ *G01N 21/534* (2013.01); *G01F 1/7086* (2013.01); *G01F 1/74* (2013.01); *G01N 2201/08* (2013.01)

(58) Field of Classification Search
CPC ............... G01P 3/36; G01P 5/20; G01P 5/18; G01N 21/534; G01N 2201/08; G01F 1/74; G01F 1/7086
USPC ....................... 356/28; 169/60, 61; 244/129.2
See application file for complete search history.

(56) References Cited

U.S. PATENT DOCUMENTS

| | | | | |
|---|---|---|---|---|
| 4,758,028 | A | 7/1988 | Davies et al. | |
| 4,866,425 | A | 9/1989 | Lindmark | |
| 4,941,778 | A * | 7/1990 | Lehmann | 406/28 |
| 5,104,735 | A | 4/1992 | Cioffi et al. | |
| 5,682,235 | A * | 10/1997 | Igushi | 356/335 |
| 6,122,575 | A | 9/2000 | Schmidt et al. | |
| 6,192,813 | B1 * | 2/2001 | Memory et al. | 111/176 |
| 6,542,234 | B1 | 4/2003 | Ulrich et al. | |
| 6,819,237 | B2 | 11/2004 | Wilson et al. | |
| 7,048,068 | B2 | 5/2006 | Paulkovich | |

(Continued)

FOREIGN PATENT DOCUMENTS

| | | |
|---|---|---|
| CN | 101858864 A | 10/2010 |
| EP | 0144018 | 6/1985 |

(Continued)

OTHER PUBLICATIONS

EP Application 12166088. European Search Report completed Nov. 12, 2012.

*Primary Examiner* — Isam Alsomiri
*Assistant Examiner* — Vicente Rodriguez
(74) *Attorney, Agent, or Firm* — Carlson, Gaskey & Olds, P.C.

(57) ABSTRACT

Disclosed is a measurement system for a dry powder agent including a nozzle to direct the dry powder agent, and an indicator operable to recognize a dry powder agent discharge event. In an exemplary method, a velocity of the powder exiting the nozzle may be computed, and an agent concentration calibration curve may be selected.

13 Claims, 12 Drawing Sheets

(56) References Cited

U.S. PATENT DOCUMENTS

| | | | | |
|---|---|---|---|---|
| 7,066,274 | B2 | 6/2006 | Lazzarini | |
| 7,080,793 | B2 | 7/2006 | Borisov et al. | |
| 7,083,000 | B2 | 8/2006 | Edwards et al. | |
| 7,087,105 | B1 | 8/2006 | Chappell et al. | |
| 7,090,028 | B2 | 8/2006 | Adiga et al. | |
| 7,093,666 | B2 | 8/2006 | Trumper | |
| 7,104,336 | B2 | 9/2006 | Ozment | |
| 7,153,446 | B2 | 12/2006 | Grigg | |
| 7,210,537 | B1 | 5/2007 | McNeil | |
| 7,232,097 | B2 | 6/2007 | Noiseux et al. | |
| 7,276,640 | B2 | 10/2007 | Mulukutla et al. | |
| 7,301,641 | B1 | 11/2007 | Overby et al. | |
| 7,333,129 | B2 | 2/2008 | Miller et al. | |
| 7,407,598 | B2 | 8/2008 | Posson et al. | |
| 7,456,750 | B2 | 11/2008 | Popp et al. | |
| 7,476,346 | B2 | 1/2009 | Hagquist et al. | |
| 2004/0012777 | A1 | 1/2004 | Vijayakumar et al. | |
| 2008/0190191 | A1 * | 8/2008 | Martin et al. | 73/167 |
| 2010/0257915 | A1 | 10/2010 | Ayers | |
| 2010/0259756 | A1 * | 10/2010 | Powell et al. | 356/437 |
| 2010/0259757 | A1 | 10/2010 | Ayers et al. | |

FOREIGN PATENT DOCUMENTS

| | | |
|---|---|---|
| EP | 0290412 | 11/1988 |
| EP | 0290413 | 11/1988 |
| WO | 2007066113 | 6/2007 |

* cited by examiner

VELOCITY SURVEY WITH POWDERIZER AND AGENT FLOW INDICATOR

RELATED APPLICATIONS

This application claims the benefit of U.S. Provisional Application No. 61/490,193, filed 26 May 2011.

BACKGROUND

The present disclosure relates to a measurement system for the measurement of dry powder based agents.

In order to certify a dry powder fire suppression system onboard a vehicle such as an aircraft, a fire extinguishing agent is discharged into the protected volume and an analyzer simultaneously records the amount of fire extinguishing agent in various zones of the protected volume. The amount of agent must be above some predetermined level which has been established sufficient to extinguish possible fires for some period of time simultaneous in all zones.

The analyzer must be calibrated and traceable such that analyzer output proves the dry powder fire suppression system is capable of extinguishing any fire within the protected space.

SUMMARY

Disclosed is a measurement system for a dry powder agent including a nozzle to direct the dry powder agent, and an indicator operable to recognize a dry powder agent discharge event. Further, in a disclosed method, a velocity of the powder exiting the nozzle may be computed, and an agent concentration calibration curve may be selected.

BRIEF DESCRIPTION OF THE DRAWINGS

Various features will become apparent to those skilled in the art from the following detailed description of the disclosed non-limiting embodiment. The drawings that accompany the detailed description can be briefly described as follows.

DETAILED DESCRIPTION

Figure 1:
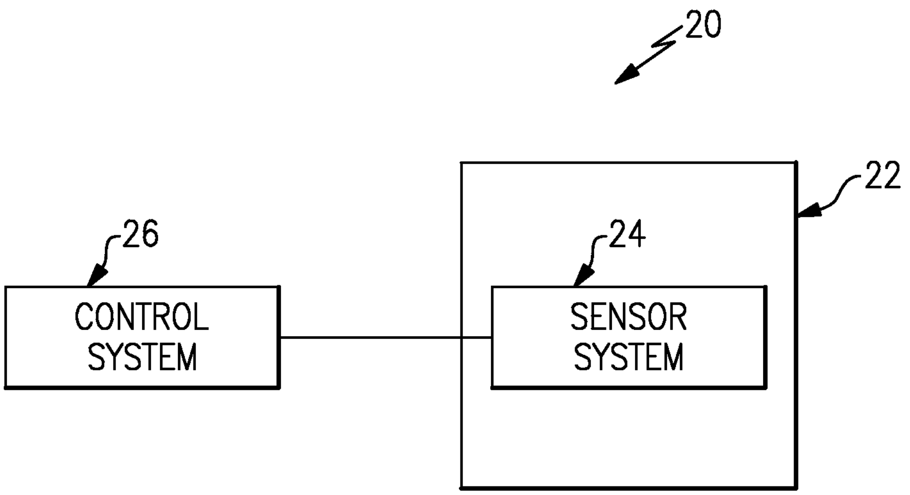
FIG. 1 is a schematic view of a measurement system with a powderizer calibration column (PCC) for a dry powder agent.
Figure 2:
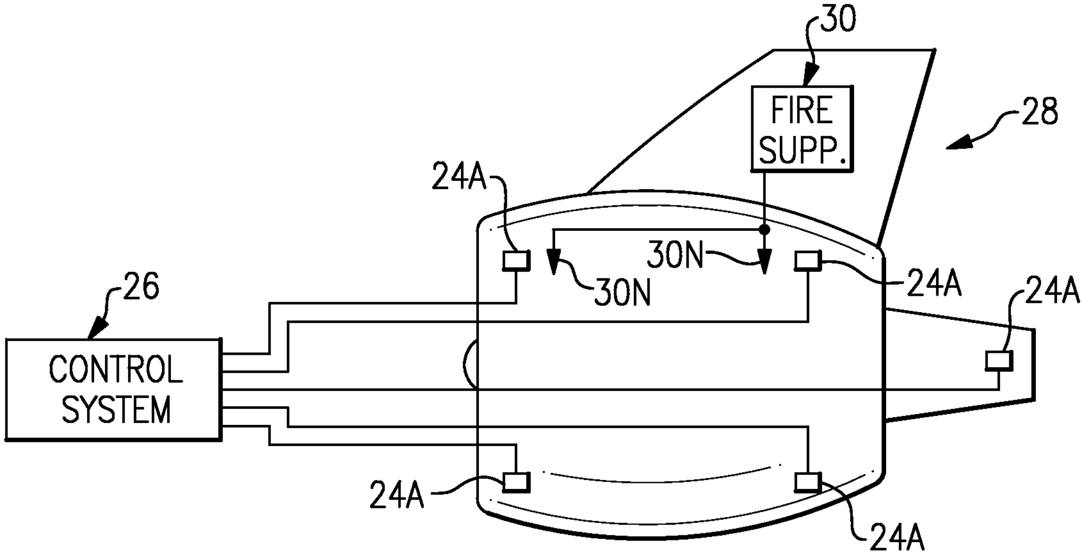
FIG. 2 is a schematic view of a sensor system for a powder based chemical fire suppressant agent installed in a representative protected structure.

FIG. 1 schematically illustrates a measurement system 20 for the measurement of dry powder agent based chemical fire suppressant agents. The system 20 generally includes a powder calibration column (PCC) 22, a sensor system 24, and a control system 26. The PCC 22 generally is utilized to calibrate a sensor of the sensor system 24 which may then be installed in a protected structure test fixture 28 such as an engine nacelle (FIG. 2). It should be understood that the engine nacelle is but one representative structure in one non-limiting embodiment, within which a powder based chemical fire suppressant system 30 having a multiple of nozzles 30N may be installed and that other protected structures 28 such as a land vehicle engine compartment, cabin or other structure will also benefit herefrom.

Figure 3A:
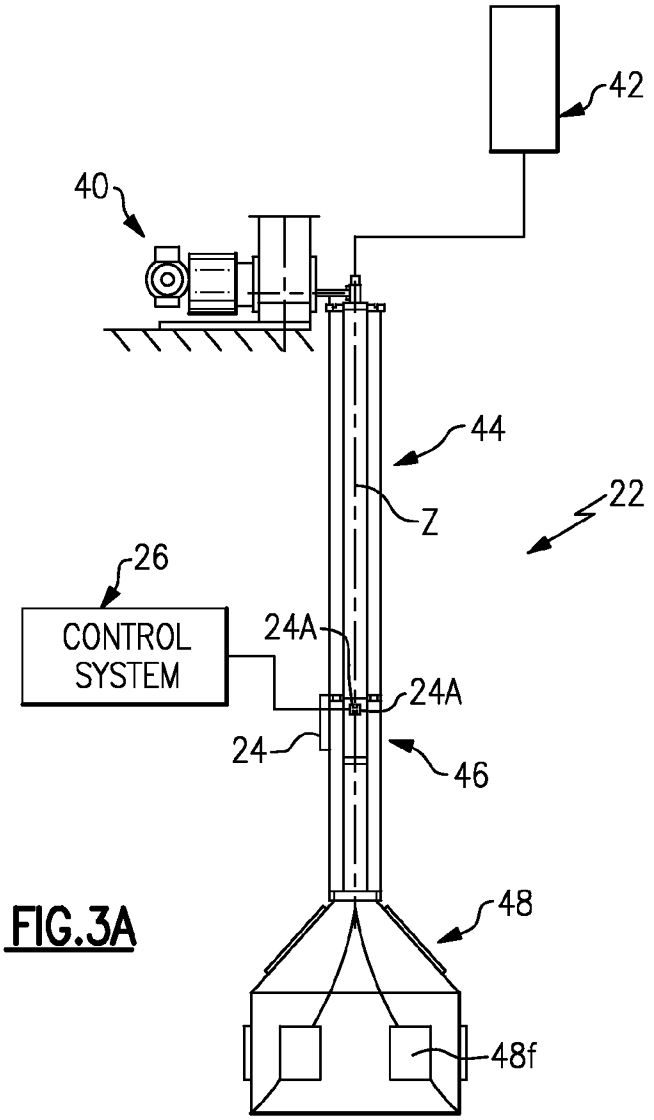
FIG. 3A is a schematic view of a powderizer calibration column (PCC) for a dry powder agent.

Referring to FIG. 3A, the PCC 22 generally includes a powder feeder system 40, a gas distribution system 42, an observation tube 44, a test section 46 within which at least one sensor head 24A, sometimes referred to as a powderizer, is mounted, and a powder capture box 48. The observation tube 44, test section 46 and powder capture box 48 are defined along an axis Z. The observation tube 44 which defines the test section 46 in one non-limiting embodiment is at least twenty diameters in length prior to the at least one sensor head 24A to ensure homogeneous distribution of the powder agent from the powder feeder system 40 and the inert gas from the gas distribution system 42. This facilitates a direct measurement of light transmission through the aerosol cloud by the sensor head 24A.

The powder feeder system 40 in one non-limiting embodiment includes an auger such as that manufactured by Acrison, Inc. of Moonachie, N.J., USA. The powder feeder system 40 defines the rate at which the dry powder agent is communicated into the observation tube 44.

Figure 3B:
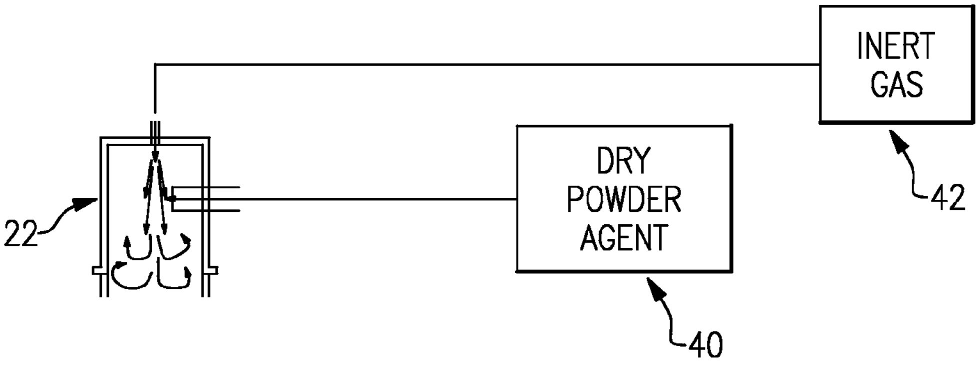
FIG. 3B is a schematic view of a powder feeder system and a gas distribution system for communication with the powderizer calibration column (PCC)

The gas distribution system 42 communicates the inert gas which, in one non-limiting embodiment, includes nitrogen to breakup and fully disperses the dry powder agent. The gas distribution system 42 is located generally above the powder feeder system 40 and transverse thereto (FIG. 3B). The gas distribution system 42 defines the rate at which the inert gas is communicated into the observation tube 44 such that a known flow of dry powder agent and inert gas are received in the sensor head 24A so that a relationship may be determined between the dry powder agent concentration and light transmission. This allows for absolute known rates of dry powder agent feed and inert gas.

The powder capture box 48 provides a relatively large volume to prevent recirculation of the powder agent back into the test section 46. The powder capture box 48 also prevents pressure build up and prevents back flow of the dry powder agent aerosol cloud facilitated by airflow outflow through filters 48F.

The PCC 22 is utilized to calibrate the sensor head 24A light transmission measurement with respect to a concentration of aerosol cloud in mass per volume. The cylindrical cross section of the PCC 22 reduces corner effects and other geometric effects. The dry powder agent is communicated into the observation tube 44 just below the inert gas introduction (FIG. 3B). The high velocity jet of inert gas passes the powder feeder system 40 to cause turbulent mixing of the dry powder agent into the inert gas flow to generate an aerosol cloud as would be typical in an aerosol cloud fire suppression agent. The process which communicates the dry powder agent into the jet of inert gas causes the dry powder agent agglomerates to break up into the principle particles. The particles mixed with the inert gas creates the dry powder agent aerosol cloud.

Figure 3C:
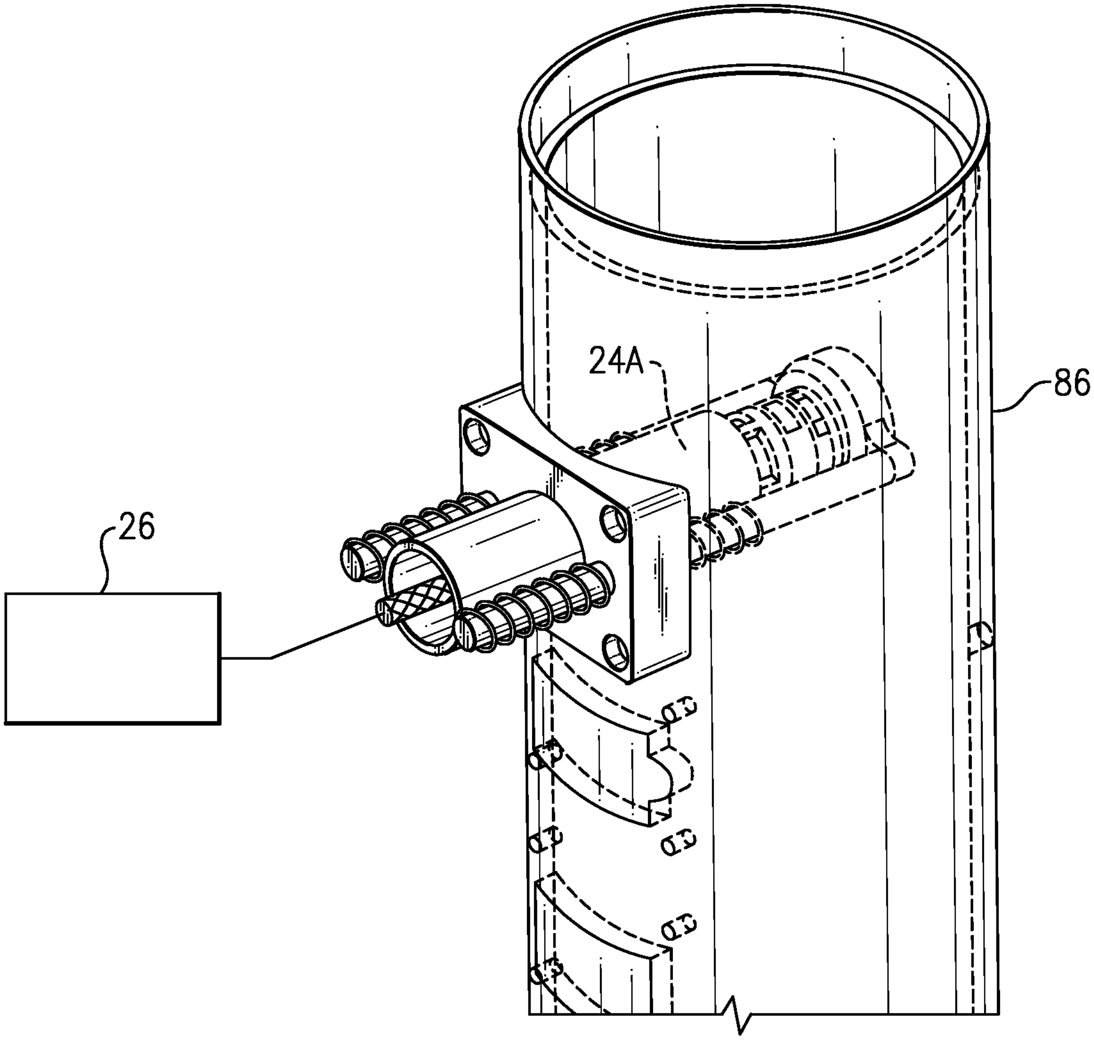
FIG. 3C is a perspective view of a sensor head within the powderizer calibration column (PCC)

The aerosol cloud travels downward with gravity in the observation tube 44 to facilitate homogeneous mixing of the aerosol cloud for measurement by the sensor head 24A (FIG. 3C). The downward flow is necessary because different sized particles of the dry powder agent travel at different velocities. Downward flow at steady conditions results in a steady-state concentration over time as the concentration of each particle size stays constant downstream to allow an accurate measurement by the sensor system 24.

Figure 4A:
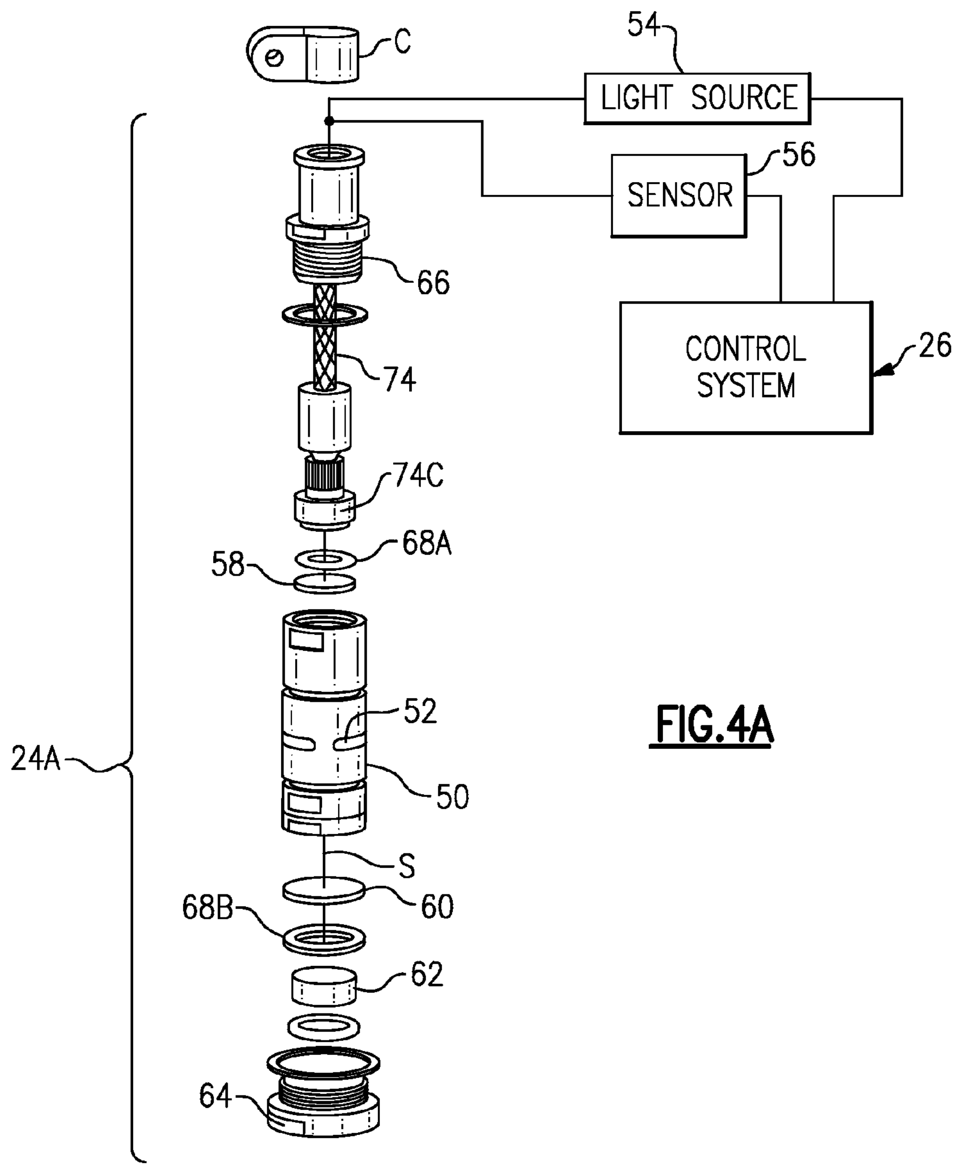
FIG. 4A is an exploded view of a sensor head for a dry powder agent.
Figure 4B:
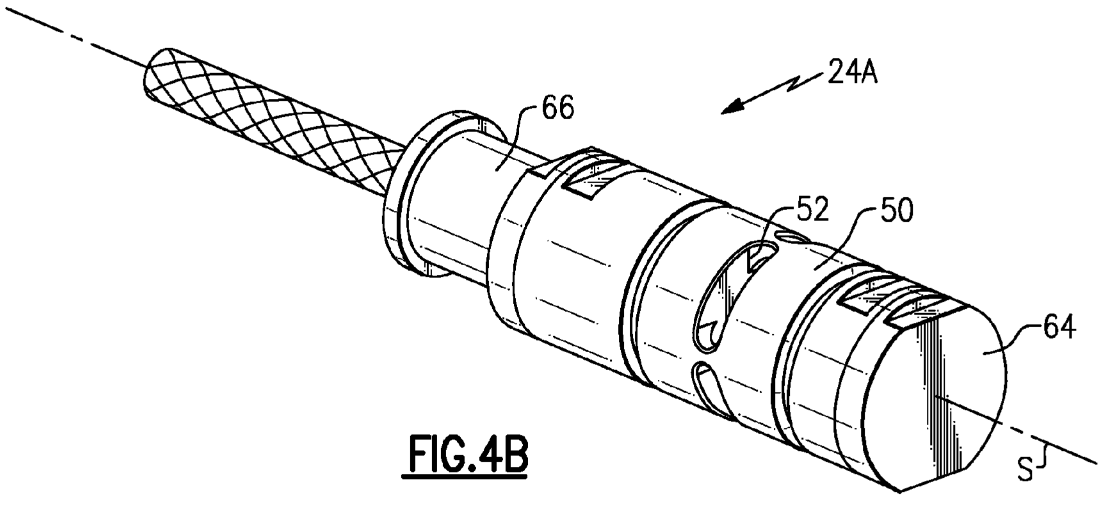
FIG. 4B is an expanded perspective view of the sensor head of FIG. 4A.

Referring to FIG. 4A, one non-limiting embodiment of the sensor head 24A provides for a light transmission measurement through the dry powder agent aerosol cloud. Each sensor head 24A generally includes a housing 50 defined along an axis S though which light is communicated along a light path and a multiple of apertures 52 transverse to the axis S (FIG. 4B). The sensor head 24A generally includes a light source 54, a detector 56, a window 58, a minor window 60, a minor 62, an end block 64, an attachment 66 and gaskets 68A, 68B.

Figure 4C:
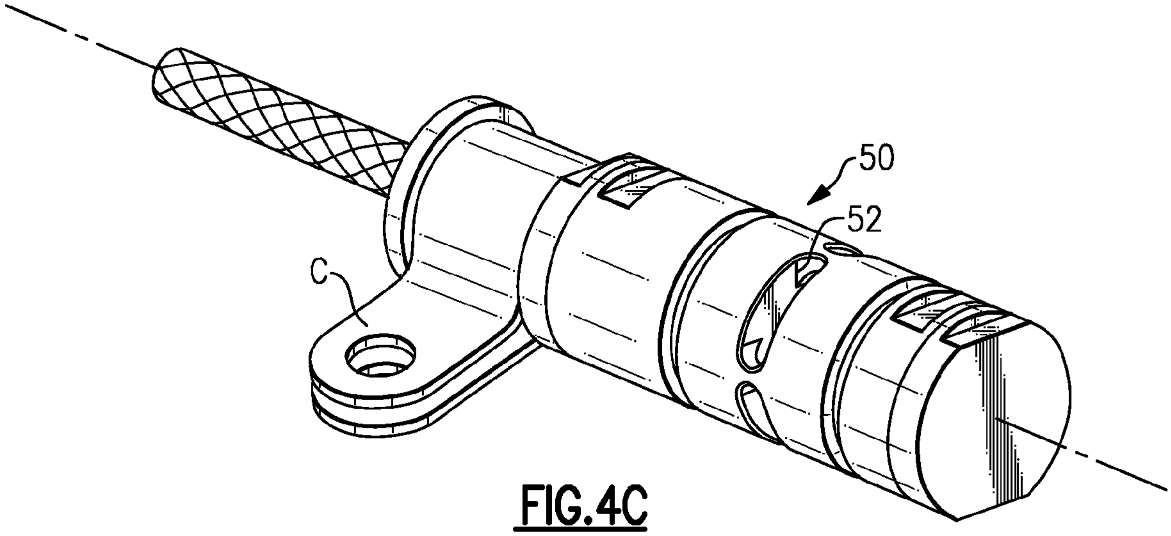
FIG. 4C is an expanded perspective view of the sensor head of FIG. 4A with a clamp attachment installed thereon.

The attachment 66 may include a flanged end to receive a clamp C or other attachment (FIG. 4C). The clamp C is readily attached within the protected structures 28 to position the sensor head 24A (FIG. 2). In one non-limiting embodiment, the gaskets 68A, 68B are gaskets (which may be electrically conductive gaskets) so as to provide an electrical ground between the window 58, the minor window 60, the mirror 62, the housing 50 and the attachment 66 through the clamp C such that the entire sensor head 24A is grounded to the protected structures 28. In this non-limiting embodiment, the housing 50, the end block 64 and the attachment 66 may be formed of a conductive material such as Aluminum coated with alodine. As the sensor head 24A is grounded, static electricity is prevented from accumulation on the window 58 and the minor window 60 to thereby minimize attraction of dry powder agent. Alternatively, or in addition thereto, the window 58 and the mirror window 60 may include an anti-static coating and may be relatively thin. In one non-limiting embodiment, each are less than 1 mm (0.04 inches) in thickness. Such a thickness minimizes distortion and reduces static electricity which may otherwise attract dry powder agent.

The gaskets 68A, 68B cushion the respective window 58 and minor window 60 in response to the end block 64 being threaded to the housing 50 and the attachment 66 being threaded to the housing 50. That is, the end block 64 and the attachment 66 are threaded into the housing 50 to permit disassembly and access to the window 58 and the mirror window 60 for cleaning or other maintenance. The threaded engagement also facilitates the coaxial alignment of the window 58, the minor window 60, and the mirror 62 such that the light source 54 will always provide for a repeatable focus on the same point on the minor 62 to assure alignment in response to the end block 64 and the attachment 66 being threaded into the housing 50. That is, the optical alignment is integral to the design.

Figure 4D:
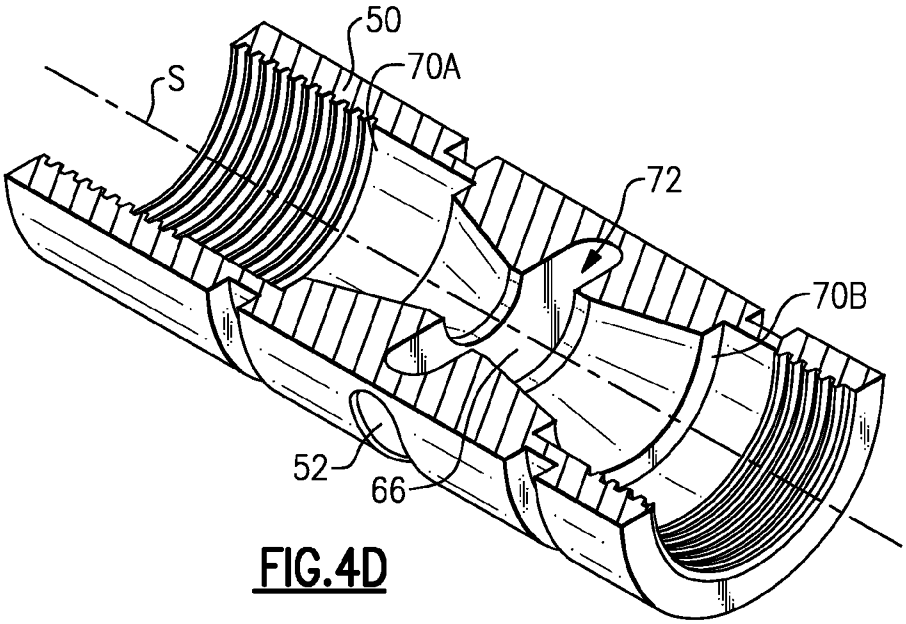
FIG. 4D is a longitudinal sectional view of the sensor head body.

A respective shoulder 70A, 70B (FIG. 4D) abuts the respective window 58 and mirror window 60 in response to the end block 64 and the attachment 66 being threaded into the housing 50. The shoulders 70A, 70B further facilitate that length repeatability of assembly such that the distance between the light source 54 and the minor 62 is repeatable. It should be understood that various gaskets, O-rings, seals, neutral density filters for calibration and combinations thereof may alternatively or additionally be provided.

The housing 50 defines a measurement volume 72 which is defined in part by the multiple of apertures 52. The measurement volume 72 is tightly maintained between the light source 54 and the mirror 62 even during the temperature changes, shock and vibration common in the protected structures 28 due to the threaded interface and shoulder 70A, 70B arrangement.

The multiple of apertures 52 are generally rectilinear and transverse to the axis S. In one non-limiting embodiment, each of the multiple of apertures 52 define a longitudinal length along the axis S which is less than a lateral length defined around the axis S, such that for example, the lateral length is less than 10 mm (0.39 inches) and more specifically, may be 3 mm (0.12 inches).

Figure 4E:
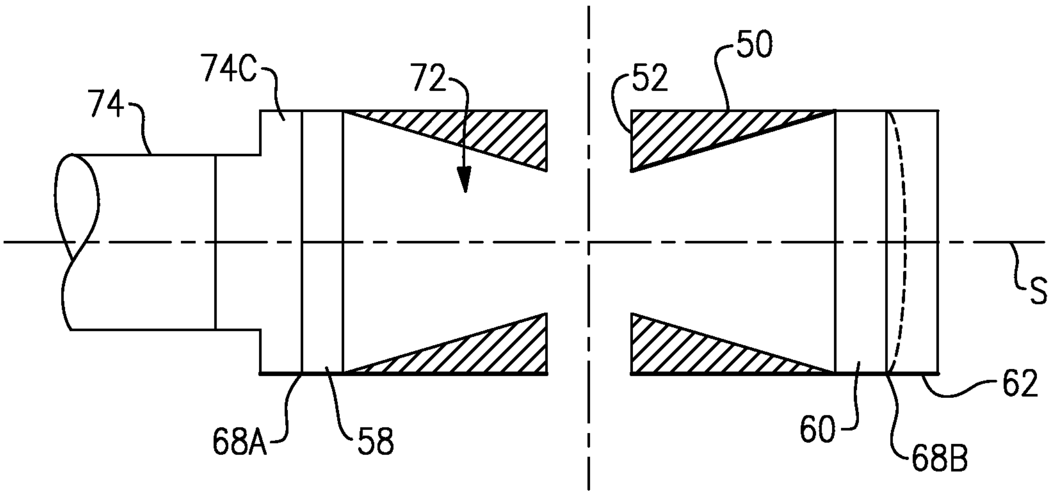
FIG. 4E is a schematic view of a measurement volume within the sensor head body.
Figure 4F:
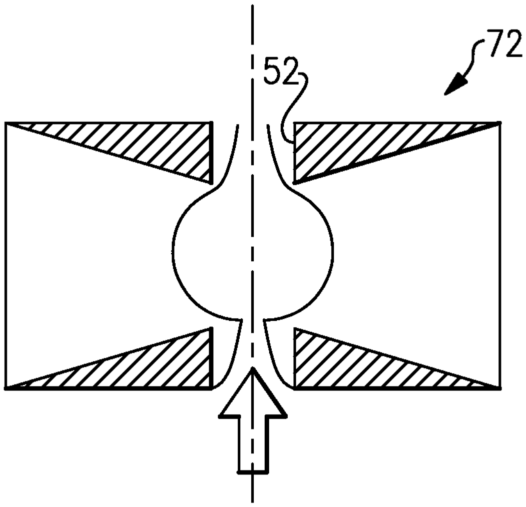
FIG. 4F is a schematic view of a concentration boundary formed by the measurement volume within the sensor head body.
Figure 4G:
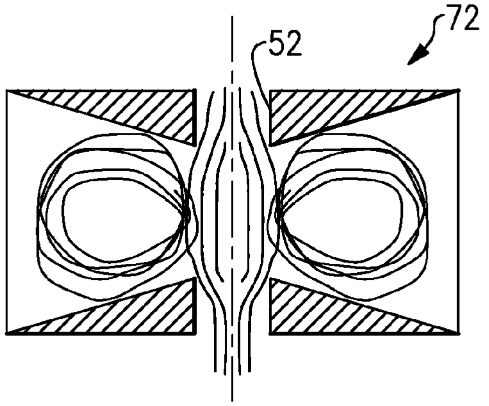
FIG. 4G is a schematic view of the stream lines which are formed generally near each the multiple of apertures within the measurement volume within the sensor head body.

Referring to FIG. 4E, the measurement volume 72 as defined in part by the multiple of apertures 52 is generally trapezoidal in shape. The shape and size of the multiple of apertures 52 readily reduces the optics contamination in high-flow and turbulent environments. The shape of the measurement volume 72 forms a concentration boundary which essentially creates a bulge of laminar flow conditions within the sensor head 24A (FIG. 4F). This is represented by the stream lines which are formed generally near each the multiple of apertures 52 (FIG. 4F).

Figure 4H:
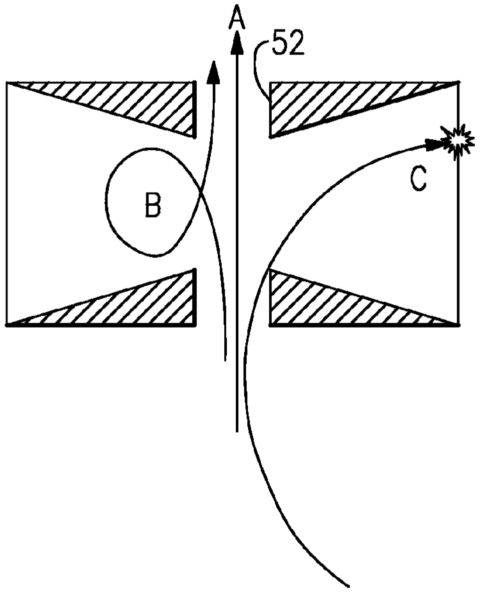
FIG. 4H is a schematic view of the primary particle paths through the multiple of apertures within the measurement volume within the sensor head body.

Bulk flow from outside the sensor head 24A enters the measurement volume 72 through the multiple of apertures 52 to create the laminar situation such that essentially no turbulence is created inside the measurement volume 72. Flow through the measurement volume 72 form a venturi effect which pulls the dry powder agent from measurement volume 72. Only a relatively small quantity of dry powder agent may be deposited on the optics via concentration gradients. More specifically, an example particle of dry powder agent from the bulk flow which enters the measurement volume 72 will either flow through the multiple of apertures 52 with minimal vector change (A); enter a cavity recirculate and be pulled out of the measurement volume 72 via venturi effects (B); or enter from a turbulent eddy and impact the optics (C) (FIG. 4H). The total amount of dry powder agent that impact the optics is relatively small and is typically less than 2% of the total mass that passed through the sensor head 24A. This does not significantly affect the concentration profile because the outside turbulence which deposits the dry powder agent onto the optics occurs over a short period compared to the concentration measurement time.

The light source 54 may include a red light emitting diode (LED) operating at 650 nm and the detector 56 is a visible spectrum photodiode. The light source 54 and the detector 56 communicate with the sensor head 24A through a fiber optic cable 74 which includes a multiple of fiber optics. In one non-limiting embodiment, 32 fiber optics communicate with the light source 54 and 32 fiber optics communicate with the detector 56. The fiber optics may be bundled to form the fiber optic cable 74 with a SMA905 connection 74C for attachment into the housing 50.

Figure 4I:
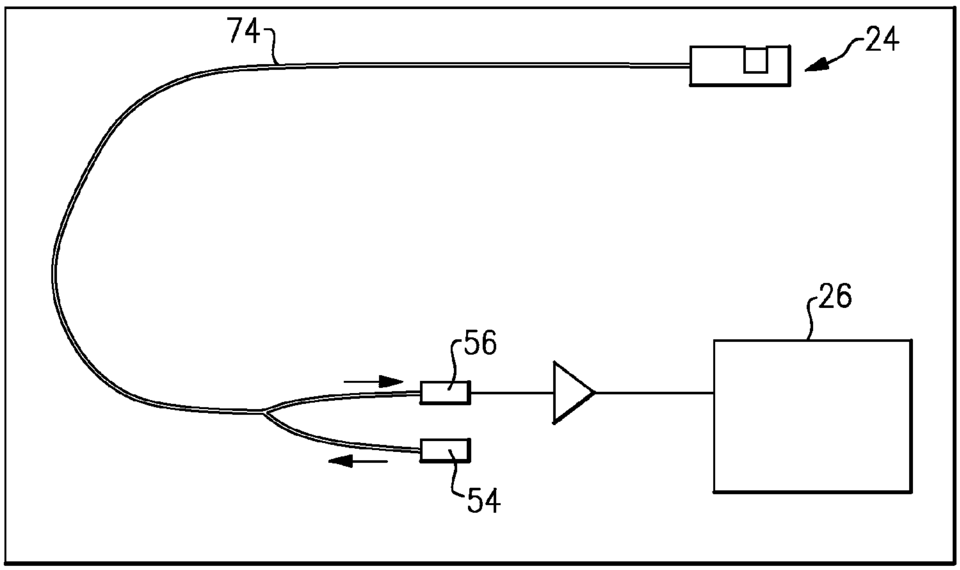
FIG. 4I is a schematic view of the sensor head in communication with a control system.

Each sensor head 24A operates on light obscuration principles. Light is communicated from the light source 54 through a multiple of fiber optics of the fiber optic cable 74, passes through the transparent windows 58 and 60, enters the measurement volume 72 in communication with the aperture 52, reflects off the minor 62 and is communicated through a multiple of the fiber optics of the fiber optic cable 74. The windows 58 and 60 are generally opposite the mirror 62 such that the light passes through the measurement volume 72 twice—from window 58 through measurement volume 72, through the window 60, reflects off mirror 62 then through window 60, measurement volume 72 and into the detector 56 via window 58 and the fiber optic cable 74. The detector 56 outputs an analog signal proportional to the intensity of light to the control system 26 (FIG. 4I). The intensity of light changes functionally to the concentration of dry powder agent particles in the measurement volume 72. The sensor head 24A is unlike thermocouples, pressure transducers, strain gauges or other instrumentation where signal strength is directly related to the phenomena being measured.

Each sensor head 24A of the sensor system 24 is in communication with the control system 26 which initiates operation of the system 20 and controls the data acquisition from the sensor head 24A. Data in one non-limiting embodiment is acquired at a variable frequency of 1 to 1000 Hz for a maximum of 30,000 total points. The maximum acquisition time is 30,000 divided by the acquisition rate (300 seconds in the case of 100 HZ). It should be understood that alternative data acquisition rates may be utilized by the control system 26.

It should be noted that a computing device can be used to implement various functionality, such as that attributable to the control system 26 (FIG. 4I). In terms of hardware architecture, such a computing device may include a processor, memory, and one or more input and/or output (I/O) device interface(s) that are communicatively coupled via a local interface. The local interface can include, for example but not limited to, one or more buses and/or other wired or wireless connections. The local interface may have additional elements, which are omitted for simplicity, such as controllers, buffers (caches), drivers, repeaters, and detectors to enable communications. Further, the local interface may include address, control, and/or data connections to enable appropriate communications among the aforementioned components.

The processor may be a hardware device for executing software, particularly software stored in memory. The processor can be a custom made or commercially available processor, a central processing unit (CPU), an auxiliary processor among several processors associated with the computing device, a semiconductor based microprocessor (in the form of a microchip or chip set) or generally any device for executing software instructions.

The memory can include any one or combination of volatile memory elements (e.g., random access memory (RAM, such as DRAM, SRAM, SDRAM, VRAM, etc.)) and/or nonvolatile memory elements (e.g., ROM, hard drive, tape, CD-ROM, etc.). Moreover, the memory may incorporate electronic, magnetic, optical, and/or other types of storage media. Note that the memory can also have a distributed architecture, where various components are situated remotely from one another, but can be accessed by the processor.

The software in the memory may include one or more separate programs, each of which includes an ordered listing of executable instructions for implementing logical functions. A system component embodied as software may also be construed as a source program, executable program (object code), script, or any other entity comprising a set of instructions to be performed. When constructed as a source program, the program is translated via a compiler, assembler, interpreter, or the like, which may or may not be included within the memory.

The Input/Output devices that may be coupled to system I/O Interface(s) may include input devices, for example but not limited to, a keyboard, mouse, scanner, microphone, camera, proximity device, etc. Further, the Input/Output devices may also include output devices, for example but not limited to, a printer, display, etc. Finally, the Input/Output devices may further include devices that communicate both as inputs and outputs, for instance but not limited to, a modulator/demodulator (modem; for accessing another device, system, or network), a radio frequency (RF) or other transceiver, a telephonic interface, a bridge, a router, etc.

When the computing device is in operation, the processor can be configured to execute software stored within the memory, to communicate data to and from the memory, and to generally control operations of the computing device pursuant to the software. Software in memory, in whole or in part, is read by the processor, perhaps buffered within the processor, and then executed.

Figure 5:
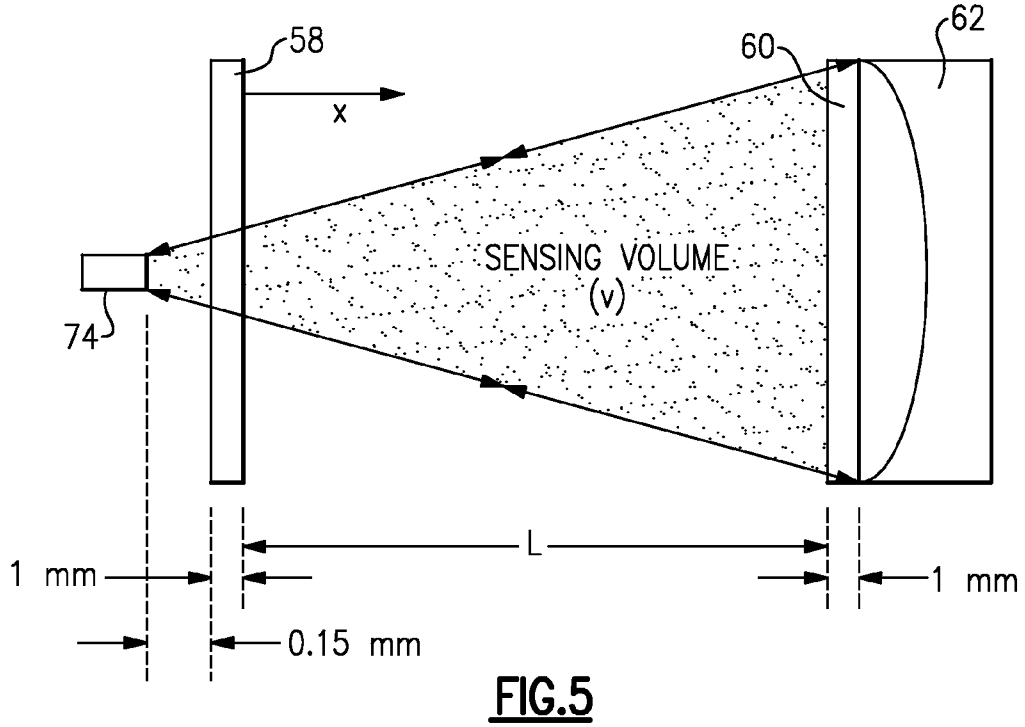
FIG. 5 is a schematic view of a sensor head sensing volume.

Referring to FIG. 5, the sensor head 24A directly measures light transmission though the dry powder agent aerosol cloud, which can be directly related to a spatial mass density concentration via an empirical or theoretical relationship.

The dry powder agent aerosol cloud enters the measurement volume 72 and passes through the light that travels from the fiber optic cable 74 to the mirror 62 and back to the detector 56. As the dry powder agent aerosol cloud passes through the light, the total light transmitted decreases proportional to the concentration of the aerosol cloud. The minor 62 is concaved and focuses the light back to the fiber optic cable 74.

Figure 6:
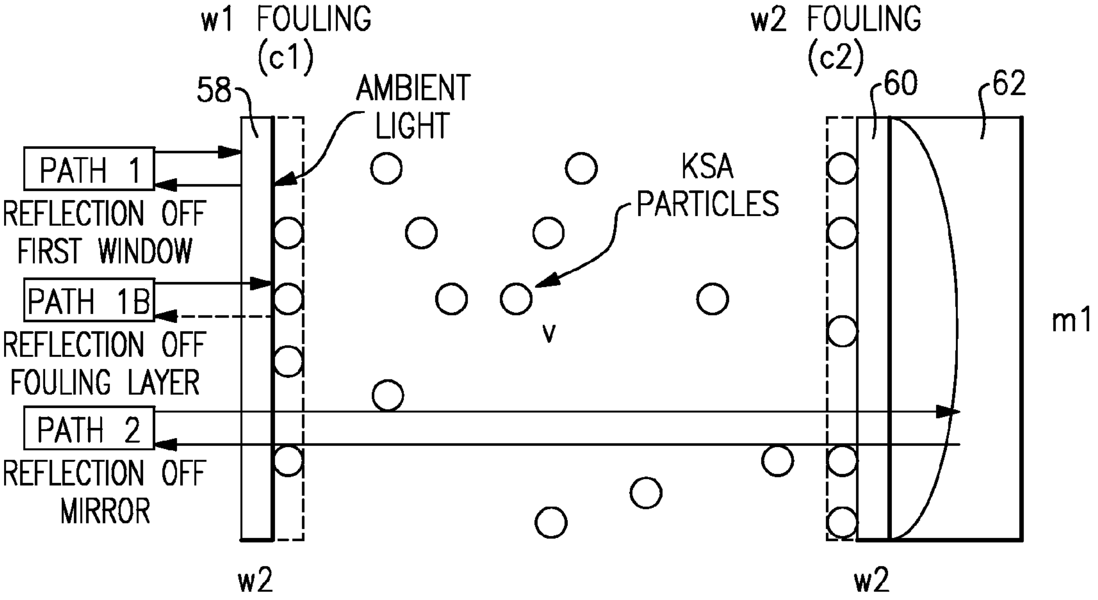
FIG. 6 is a schematic view of a sensor head sensing volume with possible light paths without multiple reflection.

Referring to FIG. 6, representative paths for the light are schematically illustrated. Reflections off of objects beyond the first fouling layer have been ignored due to the insignificant amount of light return. The intensity of light received by the detector 56 is the sum of Paths 1, 1B, 2, and the stray light from the background. In Path 1 some fraction of the reflected light off the window 58 is received. Path 1B occurs if a fouling layer exists on window 58 and must transmit through window 58 twice.

In Path 2, the light must be transmitted twice through each window 58, 60, each fouling layer, the measurement volume 72, then reflects off the mirror 62. The mirror 62 is assumed to reflect all light in these calculations. Both windows 58, 60 have the same properties.

Without a fouling layer, the sensor head 24A output can be expression as:

$$I=f_{w1}\rho_w I_s+\tau_w^4\tau_{c1}^2\tau_v^2\tau_{c2}^2 I_s+I_\infty \qquad \text{Equation 1}$$

Prior to a test, the blocked output can be measured setting $\tau_v$ to 0 by blocking the mirror 62 with non-reflective media such that only the light reflected off window 58 and ambient light are measured.

$$I_{bl}=f_{w1}\rho_w I_s+I_\infty \qquad \text{Equation 2}$$

The reference value is found when $\tau_v$ is 1, i.e. no aerosol cloud is in the measurement volume and light is allowed to reflect off the mirror back to the source. Substituting in for the measured blocked value:

$$I_{ref}=\tau_w^4\tau_{c1}^2\tau_{c2}^2 I_s+I_{bl} \qquad \text{Equation 3}$$

By substituting Equation 3 and Equation 2 into Equation 1, the double pass transmittance through the sensing volume during a test can be expressed:

$$\tau_v^2=\frac{I-I_{bl}}{I_{ref}-I_{bl}} \qquad \text{Equation 4}$$

At this point, it is convenient to define a modified sensor head 24A output with the blocked value subtracted off as the blocked value is assumed constant throughout the entire measurement.

$$I^*\equiv I-I_{bl} \qquad \text{Equation 5}$$

Equation 4 can be re-expressed:

$$\tau_v^2=\frac{I^*}{I^*_{ref}} \qquad \text{Equation 6}$$

Mass Density Concentration—Theoretical Relationship

The relationship of light transmission to concentration of particles in a dispersed cloud is given by $$\frac{di}{dx}=-n_v'''A_s i \qquad \text{Equation 7}$$

Beers' Law, squared here to give the double path transmittance, is a solution to Equation 7 where only the light intensity varies with distance.

$$\tau_v^2\equiv\left(\frac{i}{i_i}\right)^2=\exp(-2n_v'''A_sL) \qquad \text{Equation 8}$$

Equation 8 can be solved for the number density concentration, when multiplied by the mass of one particle the mass density concentration in the sensing volume is found.

$$m_v'''=\frac{1}{2L}\frac{V_p}{A_s}\rho_s\ln\left(\frac{1}{\tau_v^2}\right) \qquad \text{Equation 9}$$

The transmission through the sensing volume term is squared because the light travels through the measurement volume 72 twice. Mie Theory identifies the scattering cross sectional area as approaching twice the particle cross sectional area, as the size of the particle increases from three times the wavelength of light. In this example, the average particle diameter is above 3 μm where the wavelength of the light is 0.65 μm. Because the surface area and the mass of the individual particles are of interest, the Sauter Mean diameter is used. This is the diameter of a particle with the same surface area to mass (volume) ratio as the entire aerosol cloud population. Equation 9 reduces to a function of the Sauter Mean diameter:

$$m_v'''=\frac{1}{3}\frac{d_{[3,2]}}{2L}\rho_s\ln\left(\frac{1}{\tau_v^2}\right) \qquad \text{Equation 10}$$

Equation 10 yields a theoretical relationship between the mass density concentration and the transmission if the particle diameter has been characterized. However, this relationship is only valid at high transmissions.

Since the powderizer will measure transmissions less than that valid in Equation 9, the PCC 22 is utilized to derive an empirical relationship between transmission and spatial mass density concentration.

The experiments were conducted in the PCC 22 (FIG. 3A) which provides for constant flows of the dry powder agent and the inert gas. This provides for fully developed flow so that the dry powder agent aerosol cloud is evenly distributed across the observation tube 44 cross section. The fully mixed dry powder agent aerosol cloud then passes by the sensor head 24A where light transmission is measured. By varying the flow rate of inert gas and the feed rate of the dry powder agent, a variety of mass density concentrations could be tested.

The relationship between a transmission and spatial mass density concentration as determined in the PCC 22 is specific to the sensor head 24A design and the dry powder composition and size. If any of these change, a new relationship may be determined.

The measurement error can be found from the scatter in the transmission to spatial mass density concentration data. For the sensor head 24A in FIG. 4C, the error was found to be +/−16 g/m^3. This error would be specific to the sensor head 24A design and the dry powder composition and size.

Figure 7:
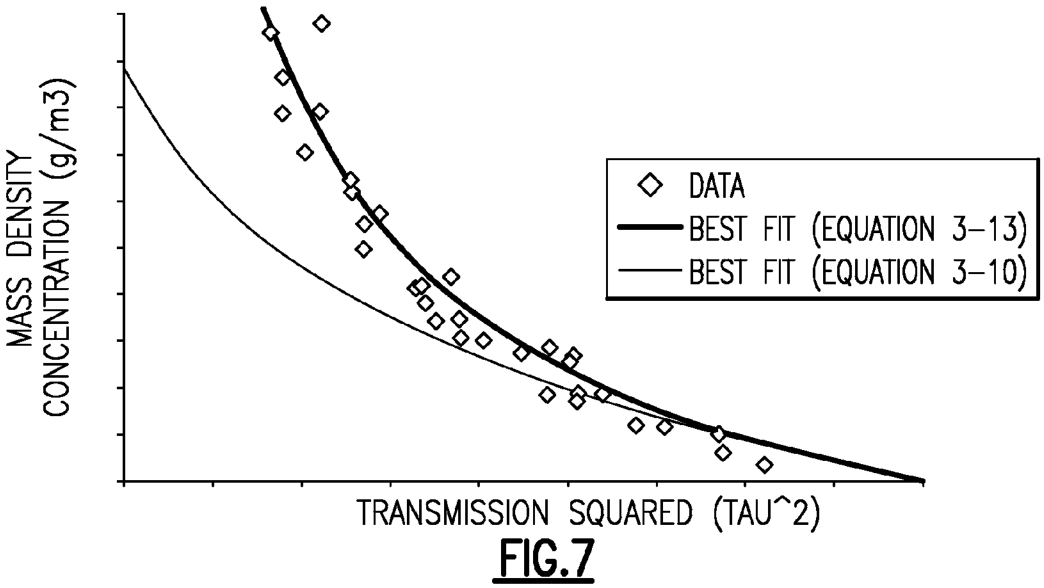
FIG. 7 is an empirical relationship between mass density concentration and light transmittance for a dry powder agent.
Figure 8:
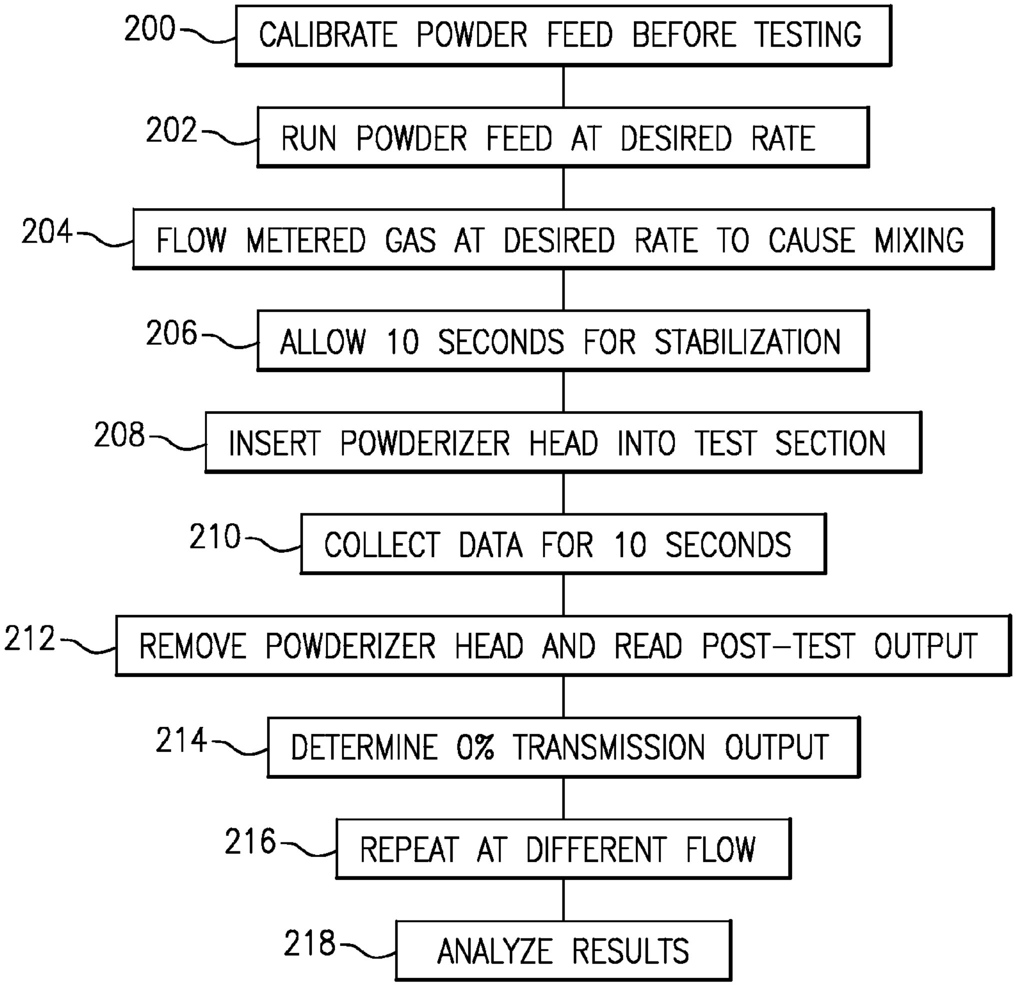
FIG. 8 is a flow chart illustrating calibration of the measurement system to determine an empirical relationship between mass density concentration and transmittance for a desired dry powder agent such as an aerosol cloud fire suppression agent.

Referring to FIG. 8, an operational example of the PCC 22 is illustrated in which the measurement system 20 is operated to determine an empirical relationship between mass density concentration and transmittance for a desired dry powder agent such as an aerosol cloud fire suppression agent (FIG. 7). In step 200, the powder feeder system 40 is calibrated to a desired dry powder agent rate. The powder feeder system 40 is then operated at the desired dry powder agent rate (g/sec) (step 202) as the gas distribution system 42 is operated at a desired inert gas rate (m3/sec) (step 204) to provide an aerosol cloud mix. A time period is then allowed for stabilization of the aerosol cloud (step 206). The desired dry powder agent rate may include, in one example, from <10 g/m3 to >300 g/m3 which may be obtained by varying auger feed rates and flow rates. The desired inert gas rate may include, in one example, bulk velocities from ~0.5 m/sec to ~3.5 m/sec with centerline velocity about 35% greater than bulk velocity.

A sensor head 24A is then inserted into the test section 46 of the PCC 22 (step 208). Data is collected from the sensor head 24A for a predetermined time period (step 210) then the sensor head 24A is removed (step 212). A zero percentage transmission in the PCC 22 from the sensor head 24A is then determined by blocking all light into the sensor head 24A with, for example, a black rubber plug (step 214). Steps 202-214 are then repeated a multiple of times to obtain data points for a curve which represents the empirical relationship between mass density concentration and transmission squared for the desired dry powder agent (Step 218; FIG. 7).

Figure 9:
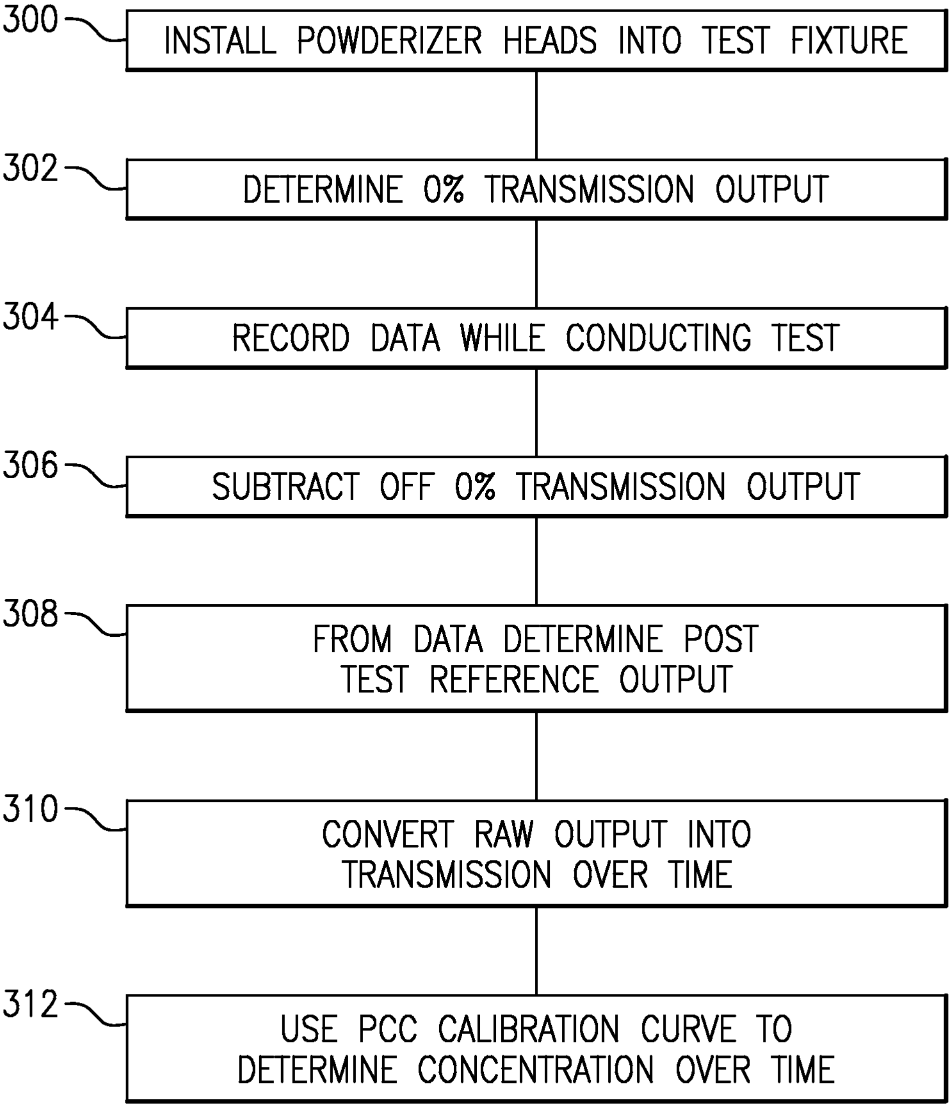
FIG. 9 is a flow chart illustrating operation of the sensor heads located within a protected structure test fixture such as the representative engine nacelle.

Referring to FIG. 9, once the empirical relationship between mass density concentration and light transmittance for the desired dry powder agent (FIG. 7) is determined, one or more sensor heads 24A may be located within a protected structure test fixture 28 such as the representative engine nacelle (FIG. 2).

In step 300, the sensor heads 24A are installed within the desired protected structure test fixture 28. A reference zero percent transmission output is determined for each sensor head 24A (step 302). That is, the difference between the zero percentage transmission in the PCC 22 and the desired protected structure test fixture 28 is determined. The aerosol cloud fire suppression agent is then activated within the protected structure test fixture 28 and data from each sensor head 24A is recorded by the control system 26 during the test (step 304). The reference zero percent transmission output is subtracted for each sensor head 24A (step 306) to determine post test reference raw output (step 308) and convert that raw output into a light transmittance over time (step 310). The sensor head is relatively small so as to be located in a remote compartment so as to measure the light transmittance of the aerosol cloud with respect to time. The light transmittance over time is then utilized with the empirical relationship between mass density concentration and transmittance for the desired dry powder agent (FIG. 7) to determine concentration over time (step 312).

Through the relatively longitudinally narrow multiple of apertures 52 normal to the optical windows, the turbulent effect of the dry powder agent discharge is significantly reduced into a laminar flow. The narrow multiple of apertures 52 allows for mostly straight aerosol trajectories. Some curved trajectories can deposit aerosol particles on the optical surfaces, however, only relatively few of the possible trajectories that can penetrate through the multiple of apertures 52. Unless an aerosol particle of the dry powder agent travels a trajectory that impacts the optics, venturi effects will carry the particle out of the sensor head 24A as the velocity through the sensing volume will tend to pull out particles of the dry powder agent.

The concentration profile across the light path within the sensing volume can be thought of as normally distributed with a higher than average concentration at the center of each of the multiple of apertures 52 which may be caused by the boundary layer effect inside the sensor head 24A tails to no concentration at the optics. Super-imposing the normal distribution onto a constant-concentration situation yields an equivalent path length. This is the path length of sensing head 24A with a constant concentration across the entire light path length. Note that the equivalent path length may be less than the opening distance due to boundary layer effects. When packets of dry powder agent deposit onto the optics, the dry powder agent will not significantly affect the area under the normal distribution such that the equivalent path length is not affected.

The sensor head 24A responds differently depending on the stream velocity moving through the measurement gap. Essentially it has a high-flow calibration curve when the stream velocity is 1.5 meters/second and above, and a low-flow calibration curve which below 1.5 meters/second. Hence it becomes important to know what the stream velocity is during agent discharge tests.

Measurements can be made using hot wire anemometers (HWA) or such, but they do not measure accurately when the gas stream contains agents, such as a KSA dry powder agent (which is a fine powder), and changes the thermal response of the heated wire. Also, the presence of a solid powder in the gas stream impacts the calibration of most measurement devices, making it difficult to interpret the results.

Figure 10:
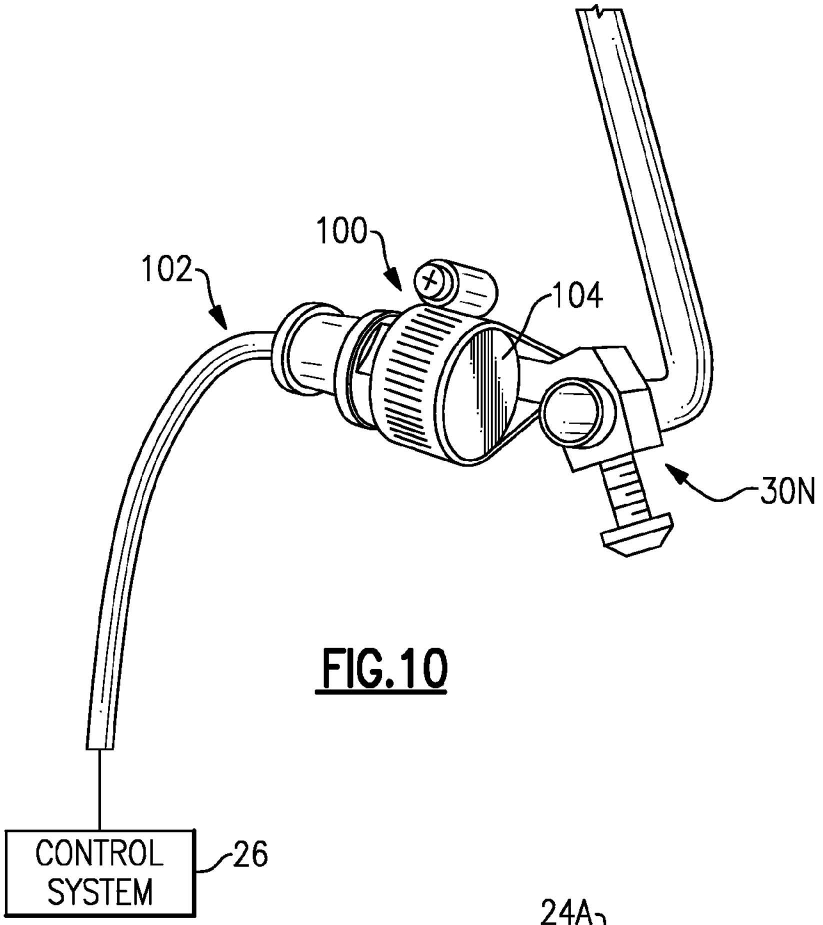
FIG. 10 is a schematic of an optical agent flow indicator adjacent to an agent nozzle.
Figure 11:
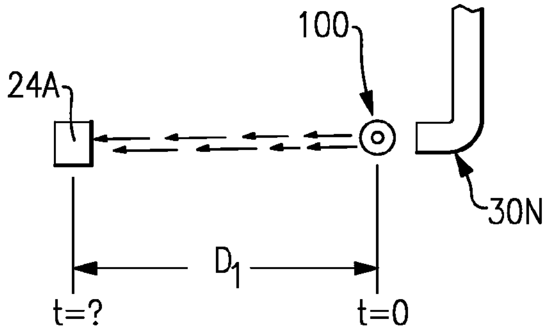
FIG. 11 is a schematic-type view illustrating the manner in which an optical flow agent indicator may be arranged relative to a sensor head and a nozzle.
Figure 12:
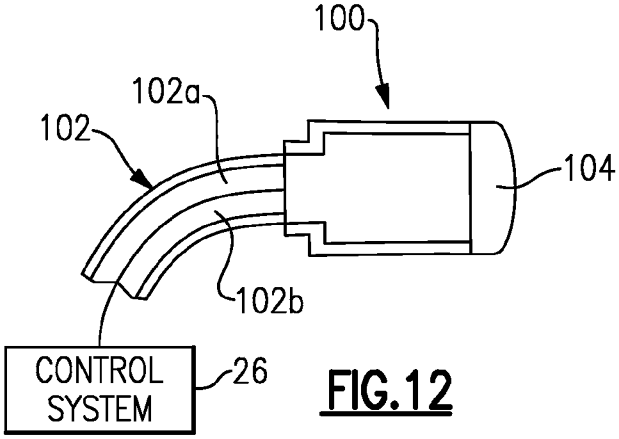
FIG. 12 is a schematic-type view of an example optical agent flow indicator.

With reference to FIG. 10, an optical agent flow indicator 100 may be utilized to directly compute the velocity of the dry powder agent through measurement of when the dry powder agent leaves the nearest discharge nozzle. In one example, each sensor head 24A is coupled with an optical agent flow indicator 100 to determine an actual agent velocity during an agent discharge event from a nozzle 30N. In this sense, the nozzles 30N are upstream of the associated sensor head 24A (e.g., as shown in FIG. 11). Further, the agent discharge event may be defined as the time when agent initially exits the nozzle 30N. Alternatively, the agent discharge event may be defined as the time when agent initially passes by the indicator 100. Notably, it should be understood that the particulars of the arrangement of the optical agent flow indicator 100 relative to the nozzle 30N shown in FIG. 10 is non-limiting, and other arrangements come within the scope of this disclosure. Further, and as explained below, the optical agent flow indicator 100 may be replaced with various non-optical indicators, as explained below relative to FIGS. 13-15.

By dividing the shortest distance from the indicator 100 and an associated sensor head 24A with the time it takes the agent to be transported therebetween (e.g., the time between the agent discharge event and the time the agent is initially recognized by the sensor head 24A), the velocity of the dry powder agent may be directly computed. For example, as represented in FIG. 11, this velocity computation entails dividing the distance $D_1$ (e.g., distance between the indicator and the associated sensor head 24A) with the time for the agent to travel from the indicator 100 (e.g., t=0, or the agent discharge event) to the sensor head 24A (e.g., t=?, or the time the agent is initially recognized by the sensor head 24A). Notably, the indicator 100 may be in communication with the control system 26, which may perform the computation.

The indicator 100 in the disclosed non-limiting embodiment is an optical based instrument, and thus the indicator 100 has a very fast response time. For example, as represented in FIG. 11, the indicator 100 includes a fiber bundle 102 and a lens 104. The lens 104 may serve to direct light reflected from the agent to the strands 102*b* in order to increase the signal reflected from the dry powder agent. However, the lens 104 is optional and need not be present.

Figure 17:
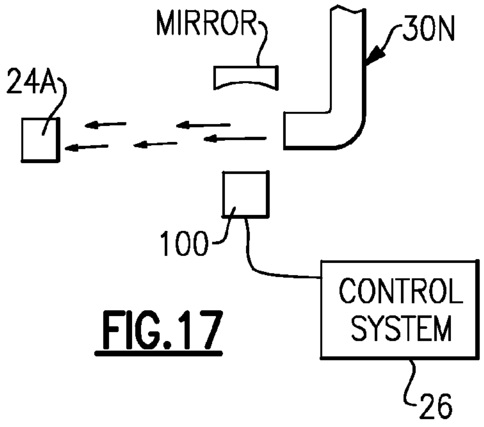
FIG. 17 is a schematic-type view illustrating an example wherein a minor is included in combination with the agent flow indicator.

The indicator 100 is operable to recognize flow out of the nozzle 30N in a manner such as the sensor head 24A, but without a mirror which sees reduced signal when light is scattered by the optically reflective Dry Powder Agent. In particular, the fiber bundle 102 may include a plurality of optical fibers, or strands, 102*a* that direct light toward the nozzle 30N, as well as a plurality of strands 102*b* configured to receive light reflected by the agent. Reflection of light back to the strands 102*b* generally indicates that agent is present, and that an agent discharge event has occurred. While minors are generally not needed in this example, mirrors may be used, as needed, to reflect signal back to the indicator 100 (schematically illustrated in FIG. 17).

Depending on the computed velocity of the agent, a calibration curve may be selected for the powder feeder 40, say. For example, if the velocity of the agent is computed as being greater than a predetermined constant, such as 1.5 m/s (approximately 3.4 mph), then a high-flow calibration curve may be selected. Likewise, in that example, an agent velocity of equal to or less than 1.5 m/s may correspond to the selection of a low-flow calibration curve.

Figure 13:
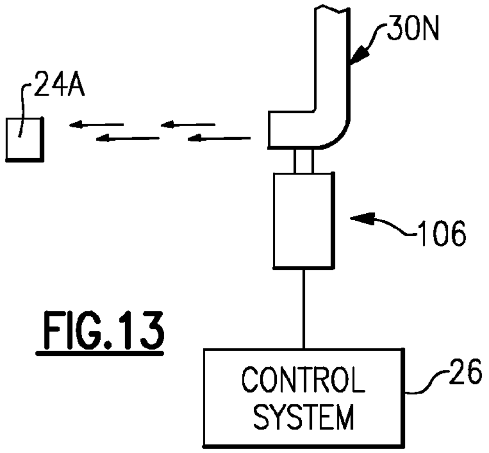
FIG. 13 is a schematic-type view illustrating an example agent flow indicator, wherein the agent flow indicator includes a pressure transducer.
Figure 14:
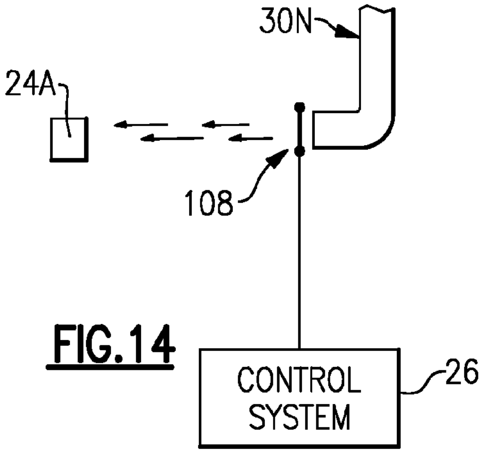
FIG. 14 is a schematic-type view illustrating another example agent flow indicator, wherein the agent flow indicator includes a break wire.
Figure 15:
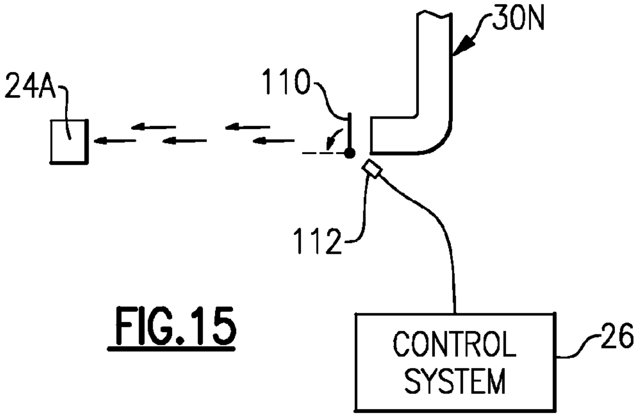
FIG. 15 is a schematic-type view illustrating yet another example agent flow indicator, wherein the agent flow indicator includes a flap assembly.

While the indicator 100 is an optical based instrument, the indicator 100 may attentively or additionally include one or more pressure transducer 106 at the nozzle exit, a break wire device 108 (which may be a wire filament or some type of foil), or a flap assembly (including a flapper 110 with a microswitch 112), as generally represented in FIGS. 13-15, respectively. Further, while the indicator 100 shown in FIG. 10 is positioned relatively close to the nozzle 30N, the indicator 100 may be positioned at any point between the nozzle 30N and the associated sensor head 24A.

Figure 16:
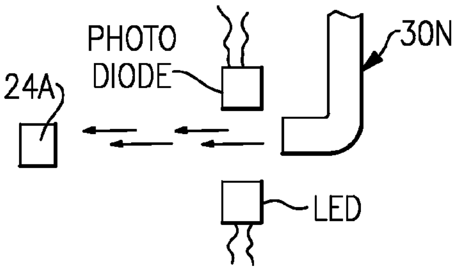
FIG. 16 is a schematic-type view illustrating yet another example agent flow indicator, wherein the agent flow indicator includes an LED/photodiode couple.

It is also possible to include an LED/photodiode couple (schematically illustrated in FIG. 16), which would be positioned to look across the outlet of the nozzle 30N (e.g., an LED would be positioned on one side of the stream with a photodiode positioned opposite the LED). Dry powder agent passing through the gap between the LED and the photodiode will reduce the signal therebetween, indicating a discharge event. Further, the LED/photodiode couple may be fiber optically coupled from a measurement point, in order to the remove the LED/photodiode couple from the potentially hot environment.

The following tables are included to clarify, to the extent needed, the nomenclature used throughout this application.

Nomenclature

| SYMBOL | DESCRIPTION | UNITS |
|---|---|---|
| $A_s$ | Scattering cross sectional area of a particle | $m^2$ |
| d | Diameter | m |
| f | Fraction | — |
| i | Intensity | lux |
| I | Sensor head 24 A output | Volts |
| L | Path length of light | m |
| m | Mass | kg |
| n | Number | — |
| V | Volume | $m^3$ |
| x | Dimensional displacement | m |
| ρ | Density | $g/m^3$ |
| $\rho_w$ | Window reflection | — |
| τ | Transmission | — |

Nomenclature

| SUBSCRIPT | DESCRIPTION |
|---|---|
| ∞ | Ambient |
| [3, 2] | Sauter mean |
| bl | Blocked |
| c | Fouling layer |
| i | Initial |
| p | Particle |
| ref | Reference |
| s | Source, Solid, or Scattering |
| v | Sensing volume |
| w | Window |

Nomenclature

| SUPERSCRIPT | DESCRIPTION | UNITS |
|---|---|---|
| ''' | Per volume (density concentration) | $1/m^3$ |
| * | Modified sensor head 24 A output (blocked output subtracted off) | |

It should be understood that relative positional terms such as "forward," "aft," "upper," "lower," "above," "below," and the like are with reference to the normal operational attitude of the vehicle and should not be considered otherwise limiting.

It should be understood that like reference numerals identify corresponding or similar elements throughout the several drawings. It should also be understood that although a particular component arrangement is disclosed in the illustrated embodiment, other arrangements will benefit herefrom.

Although particular step sequences are shown, described, and claimed, it should be understood that steps may be performed in any order, separated or combined unless otherwise indicated and will still benefit from the present disclosure.

One of ordinary skill in this art would understand that the above-described embodiments are exemplary and non-limiting. That is, modifications of this disclosure would come within the scope of the claims. Accordingly, the following claims should be studied to determine their true scope and content.

What is claimed is:

1. A measurement system for a dry powder agent comprising:
- a nozzle to direct a dry powder agent;
- an indicator operable to recognize a dry powder agent discharge event;
- a control system operable to compute a velocity of the dry powder agent;
- wherein the nozzle is arranged to direct the dry powder agent downstream to a sensor head such that the dry powder agent flows past the indicator before reaching the sensor head;
- wherein the control system is operable to compute the velocity of the dry powder agent by dividing a time it takes the dry powder agent to initially pass from the indicator to the sensor head with a distance between the indicator and the sensor head;
- wherein the indicator is an optical agent flow indicator; and
- wherein the control system is operable to calibrate a powder feeder based on the computed velocity, and wherein the control system is operable to calibrate the powder feed by selecting one of a high-flow calibration curve and a low-flow calibration curve.

2. The system as recited in claim 1, wherein the optical agent flow indicator recognizes the dry powder agent discharge event either with or without the use of mirrors.

3. The system as recited in claim 1, wherein the optical agent flow indicator includes a plurality of first and second fiber strands, the first strands operable to direct light toward the nozzle, the second strands operable to receive light reflected by the dry powder agent.

4. The system as recited in claim 3, wherein the optical agent flow indicator further includes a lens positioned between the first and second fiber strands and the nozzle.

5. The system as recited in claim 1, wherein the velocity of the dry powder agent is computed based, in part, on a reading from the optical agent flow indicator and a reading from the sensor head.

6. The system as recited in claim 1, wherein the sensor head includes a powderizer.

7. A method comprising the following steps:

feeding a dry powder agent from an exit nozzle downstream to a sensor head such that the dry powder agent flows past an optical flow indicator before reaching the sensor head;

computing a velocity of the powder exiting the nozzle by dividing a time it takes the dry powder agent to pass from the optical flow indicator to the sensor head with a distance between the optical flow indicator and the sensor head; and calibrating a powder feeder based on the computed velocity, wherein the step of calibrating the powder feeder includes selecting one of a high-flow calibration curve and a low-flow calibration curve.

8. The method as recited in claim 7, further including:

providing a flow of the dry powder agent to the nozzle using a powder feeding system positioned upstream of the nozzle.

9. The method as recited in claim 8, wherein the powder feeding system includes an auger.

10. The method as recited in claim 7, wherein the high-flow calibration curve is selected when the computed velocity is greater than a predetermined flow rate, and wherein the low-flow calibration curve is selected when the computed velocity is equal to or less than the predetermined flow rate.

11. The method as recited in claim 10, wherein the predetermined flow rate is 1.5 meters per second (m/s).

12. The system as recited in claim 1, wherein the control system is operable to select the high-flow calibration curve when the computed velocity is greater than a predetermined flow rate, and wherein the control system is operable to select the low-flow calibration curve when the computed velocity is equal to or less than the predetermined flow rate.

13. The system as recited in claim 12, wherein the predetermined flow rate is 1.5 meters per second (m/s).

* * * * *